:::
United States Patent [19]

Gordon et al.

[11] Patent Number: 5,917,124
[45] Date of Patent: Jun. 29, 1999

[54] TRANSGENIC MOUSE MODEL OF PROSTATE CANCER

[75] Inventors: Jeffrey I. Gordon, Olivette; Emily M. Garabedian, St. Louis, both of Mo.

[73] Assignee: Washington University, St. Louis, Mo.

[21] Appl. No.: 08/927,986

[22] Filed: Sep. 12, 1997

[51] Int. Cl.$^6$ ........................................................ A61F 2/30
[52] U.S. Cl. .................................. 800/18; 800/2; 800/10; 800/3; 800/21; 800/25; 435/172; 435/69.1; 435/320.1; 435/325; 435/455; 424/9.21
[58] Field of Search ................................... 800/2, 18, 10, 800/3, 21, 25; 435/172.3, 69.1, 320.1, 325, 455; 424/9.21

[56] References Cited

PUBLICATIONS

Houdebine, Journal of Biotechnology, vol. 34, pp. 269–287 1994.
Wall, Theriogenology, vol. 45, pp. 57–68 1996.
Kappel et al., Current Opinion in Biotechnology, vol. 3, pp. 548–553 1992.
Srojek & Wagner, Genetic Engineering: Principles and Methods, vol. 10, pp. 221–246 1988.
Ebert et al., Molecular Endocrinology, vol. 2, pp. 277–283 1988.
Hammer et al., Journal of Animal Science, vol. 63, pp. 269–278 1988.
Bjerknes et al., "The stem–cell zone of the small intestine epithelium. II Evidence from paneth cells in the newborn mouse" *Am. J. Anat.* 160:65–75 (1981).
Bjerknes et al., "Clonality of dysplastic epithelium in colorectal adenomas from familial adenomatous polyposis patients" *Cancer Res.* 57:355–361 (1997).
Bonasera et al., "Preclinical evaluation of fluorine–18–labeled androgen receptor ligands in baboons" *J. Nuclear Med.* 37:1009–1015 (1996).
Bonkhoff, "Role of the basal cells in premalignant changes of the human prostate: A stem cell concept for the development of prostate cancer" *Eur. Urol.* 30:201–205 (1996).
Bonkhoff et al., "Differentiation pathways and histogenetic aspects of normal and abnormal prostatic growth: A stem cell model" *Prostate* 28:98–106 (1996).
Brawer, "Prostatic intraepithelial neoplasia: A premalignant lesion" *Human Pathology* 23(3) 242–248 (1992).
Bry et al., "Paneth cell differentiation in the developing intestine of normal and transgenic mice" *Proc. Natl. Acad. Sci. USA* 91:10335–10339 (1994).
Bry et al., "A model of host–microbial interactions in an open mammalian ecosystem" *Science* 273:1380–1383 (1996).
Chandrasekaran et al., "Use of normal and transgenic mice to examine the relationship between terminal differentiation of intestinal epithelial cells and accumulation of their cell cycle regulators" *J. Biol. Chem.* 271:28414–28421 (1996).
Cheng et al., "Origin, differentiation and renewal of the four main epithelial cell types in the mouse small intestine. I Columnar cell" *Am. J. Anat.* 141:461–480 (1974).

Cohen et al., "Immunohistochemical detection of oncogene proteins and neuroendocrine differentiation in different stages of prostate cancer" *Pathology* 27:229–232 (1995).
Cohn et al., "The use of antibodies to 5–bromo–2'–deoxyuridine for the isolation of DNA sequences containing excision–repair sites" *J. Biol. Chem.* 259:12456–12462 (1984).
Colombel et al., "Detection of the apoptosis–suppressing oncoprotein bcl–2 in hormone–refractory human prostate cancers" *Am. J. Path.* 143:390–400 (1993).
di Sant'Agnese et al., "Neuroendocrine differentiation in prostatic malignancy" *Cancer* 78:357–361 (1996).
Dietrich et al., "Genetic identification of Mom–1, a major modifier locus affecting Min–induced intestinal neoplasia in the mouse" *Cell* 75:631–639 (1993).
Ewald et al., "Time–sensitive reversal of hyperplasia in transgenic mice expressing SV/40 T antigen" *Science* 273:1384–1386 (1996).
Falk et al., "Lectins are sensitive tools for defining the differentiation programs of mouse gut epithelial cell lineages" *Am. J. Physiol.* (*Gastrointest. Liver Physiol.*) 266, 987–1003 (1994).
Ferraris et al., "Polyclonal origin of medullary carcinoma of the thyroid in multiple endocrine neoplasia type 2" *Hum. Genet.* 99:202–205 (1997).

(List continued on next page.)

*Primary Examiner*—Deborah Crouch
*Assistant Examiner*—Jill D. Martin
*Attorney, Agent, or Firm*—Arnall Golden & Gregory, LLP

[57] ABSTRACT

Disclosed are transgenic mice that produces prostate tumors and faithfully recapitulate many of the features of human prostatic carcinoma. It has been discovered that transcriptional regulatory elements active in Paneth cells, granule goblet cells, intermediate cells, or a combination, when used to express Simian Virus 40 large T antigen (TAg) in a transgenic mouse leads to development of prostate tumors in the mouse. The transcriptional regulatory elements are derived from the cryptdin-2 (CR2) gene. The disclosed mice develop prostatic intraepithelial neoplasia (PIN) at an early age. Progression with local invasion, loss of androgen-dependence and eventual metastases are hallmarks of the disclosed transgenic mice. Preferred embodiments of the disclosed transgenic mice have several important characteristics: (1) the disease is fully penetrant—all mice containing the SV40 TAg transgene develop prostatic cancer; (2) the first appearance of SV40 TAg always coincides with the appearance of cellular atypia in prostatic acini; (3) the rate of progression of the neoplasia is rapid; (4) prostatic adenocarcinomas in the transgenic mice exhibit foci of neuroendocrine differentiation; (5) metastatic lesions are common in the lymph nodes, liver, lung, and bone of the disclosed transgenic mice and are evident early in life; and (6) the lifespan of the disclosed transgenic animals is not shortened by transgene-related pathology in other organs—female transgenic mice develop normally and have a normal lifespan.

17 Claims, No Drawings

PUBLICATIONS

Gaspar et al., "A single base deletion in the Tfm androgen receptor gene creates a short–lived messenger RNA that directs internal translation initiation" *Proc. Natl. Acad. Sci. USA* 88:8606–8610 (1991).

Gavrieli et al., "Identification of programmed cell death in situ via specific labeling of nuclear DNA fragmentation" *J. Cell Biol.* 119:493–501 (1992).

Gingrich et al., "Metastatic prostate cancer in a transgenic mouse" *Cancer Res.* 61 56:4096–4102 (1996).

Gould et al., "Mom1 is a semi–dominant modifier of intestinal adenoma size and multiplicity in Min/+mice" *Genetics* 144:1769–1776 (1996).

Greenberg et al. "Prostate cancer in a transgenic mouse" *Proc. Natl. Acad. Sci. USA* 92:3439–3443 (1995).

Hall et al., "Regulation of cell number in the mammalian gastrointestinal tract: The importance of apoptosis" *J. Cell Sci.* 107:3569–3577 (1994).

Hammer et al., "Spontaneous inflammatory disease in transgenic rats expressing HLA–B27 and human $\beta_2$m: An animal model of HLA–B27–associated human disorders" *Cell* 63:1099–1112 (1990).

Hauft et al., "Expression of SV–40 T antigen in the small intestinal epithelium of transgenic mice results in proliferative changes in the crypt and reentry of villus–associated enterocytes into the cell cycle but has no apparent effect on cellular differentiation programs and does not cause neoplastic transformation" *J. Cell Biol.* 117:825–839 (1992).

He et al., "A frame–shift mutation in the androgen receptor gene causes complete androgen insensitivity in the testicular–feminized mouse" *Nucleic Acids Res.* 19:2373–2378 (1991).

Homma et al., "Inhibition of rat prostate carcinogenesis by a 5α–reductase inhibitor, FK143" *J. Natl. Cancer Inst.* 89:803–807 (1997).

Huttner et al., "Structure and diversity of the murine cryptdin gene family" *Genomics* 19:448–453 (1994).

Isaacs et al., "The role of androgen in the regulation of programmed cell death/apoptosis in normal and malignant prostatic tissue" *Seminars in Cancer Biol.* 5:391–400 (1994).

Isaacs et al., "Adaptation versus selection as the mechanism responsible for the relapse of prostatic cancer to androgen ablation therapy as studied in the Dunning R–3327–H adenocarcinoma" *Cancer Res.* 41:5070–5075 (1981).

Karp et al., "Prostate cancer prevention: Investigational approaches and opportunities" *Cancer Res.* 56:5547–5556 (1996).

Lew et al., "GHF–1–promoter–targeted immortalization of a somatotropic progenitor cell results in dwarfism in transgenic mice" *Genes Dev.* 7:683–693 (1993).

Lewin et al., "Genes V" (Oxford University Press, Oxford) pp. 847–873.

Li et al., "Simian virus 40 T antigen–induced amplification of pre–parietal cells in transgenic mice" *J. Biol. Chem.* 270:15777–15788 (1995).

Loeffler et al., "Somatic mutation, monoclonality and stochastic models of stem cell organization in the intestinal crypt" *Theor. Biol.* 160:471–491 (1993).

MacPhee et al., "The secretory phospholipase A2 gene is a candidate for the Mom1 locus, a major modifier of Apc$^{Min}$– induced intestinal neoplasia" *Cell* 81:957–966 (1995).

Maroulakou et al., "Prostate and mammary adenocarcinoma in transgenic mice carrying a rat C3(1) simian virus 40 large tumor antigen fusion gene" *Proc. Natl. Acad. Sci. USA* 91:11236–11240 (1994).

Maxwell et al., "Cloning, sequence determination, and expression in transfected cells of the coding sequence for the tox 176 attenuated diphtheria toxin A chain" *Mol. Cell. Biol.* 7:1576–1579 (1987).

McCarthy et al., "Nuclear medicine and positron emission tomography: An overview" *J. Chem. Ed.* 71:830–836 (1994).

McDonnell et al., "Expression of the protooncogene bcl–2 in the prostate and its association with emergence of androgen–independent prostate cancer" *Cancer Res.* 52:6940–6944 (1992).

Moser et al., "A dominant mutation that predisposes to multiple intestinal neoplasia in the mouse" *Science* 247:322–324 (1990).

Mulherkar et al., "Expression of enhancing factor gene and its localization in mouse tissues" *Histochem.* 96:367–370 (1991).

Mulherkar et al., "Enhancing factor, a paneth cell specific protein from mouse small intestines: Predicted amino acid sequence from RT–PCR amplified cDNA and its expression" *Biochem. Biophys. Res. Comm.* 195:1254–1263 (1993).

Ohmura et al., "A possible multiclonal development in colonic carcinomas" *J. Cancer Res. & Clin. Onc.* 121:321–326 (1995).

Palmiter et al., "Dramatic growth of mice that develop from eggs microinjected with metallothionein–growth hormone fusion genes" *Nature* 300:611–615 (1982).

Pandis et al., "Chromosome abnormalities in bilateral breast carcinomas" *Cancer* 76:250–258 (1995).

Perez–Stable et al., "Prostate, adrenocortical, and brown adipose tumors in fetal globin/T antigen transgenic mice" *Lab Invest.* 74:363–373 (1996).

Perez–Stable et al., "Prostate cancer progression, metastatics, and gene expression in transgenic mice" *Cancer Res.* 57:900–906 (1997).

Raffo et al., "Overexpression of bcl–2 protects prostate cancer cells from apoptosis in vitro and confers resistance to androgen depletion in vivo" *Cancer Res.* 55:4438–4445 (1995).

Randall, "Role of 5α–reductase in health and disease" *Baillière's Clin. Endo. Metabol.* 8:405–431 (1994).

Rennie et al., "Loss of androgen dependence is associated with an increase in tumorigenic stem cells and resistance to cell–death genes" *J. Steroid Biochem. Molec. Biol.* 37:843–847 (1990).

Roth et al., "Mapping enteroendocrine cell populations in transgenic mice reveals an unexpected degree of complexity in cellular differentiation within the gastrointestinal tract" *J. Cell Biol.* 110:1791–1801 (1990).

Rouleau et al., "Ductal heterogeneity of cytokeratins, gene expression, and cell death in the rat ventral prostate" *Mol. Endocrinol.* 4:2003–2013 (1990).

Segal et al., "BCL–2 proto–oncogene expression in prostate cancer and its relationship to the prostatic neuroendocrine cell" *Arch. Pathol. Lab Med.* 118:616–618 (1994).

Selsted et al., "Enteric defensins: Antibiotic peptide components of intestinal host defense" *J. Cell. Biol.* 118:929–936 (1992).

Shibata et al., "Progression of prostatic intraepithelial neoplasia to invasive carcinoma in C3(1)/SV40 large T antigen transgenic mice: Histopathological and molecular biological alterations" *Cancer Res.* 56:4894–4903 (1996).

Simon et al., "A 20–nucleotide element in the intestinal fatty acid binding protein gene modulates its cell lineage–specific, differentiation–dependent, and cephalocaudal patterns of expression in transgenic mice" *Proc. Natl. Acad. Sci. USA* 92:8685–8689 (1995).

Sluyser, "Hormone resistance in cancer: The role of abnormal steroid receptors" *Crit. Rev. Onc.* 5:539–554 (1994).

Su et al., "Multiple intestinal neoplasia caused by a mutation in the murine homolog of the APC gene" *Science* 256:668–670 (1992).

Wyllie et al., "Cell death: The significance of apoptosis" *Int. Rev. Cytol.* 68:251–306 (1980).

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 19 base pairs
      (B) TYPE: nucleic acid
      (C) STRANDEDNESS: single
      (D) TOPOLOGY: linear (ii) MOLECULE TYPE: DNA (iii) HYPOTHETICAL: NO (iv) ANTI-SENSE: no (xi) SEQUENCE DESCRIPTION: SEQ ID NO:1:

ATGAATGGGA GCAGTGGTG          19

(2) INFORMATION FOR SEQ ID NO:2:

(i) SEQUENCE CHARACTERISTICS:
      (A) LENGTH: 23 base pairs
      (B) TYPE: nucleic acid
      (C) STRANDEDNESS: single
      (D) TOPOLOGY: linear (ii) MOLECULE TYPE: DNA (iii) HYPOTHETICAL: NO (iv) ANTI-SENSE: no (xi) SEQUENCE DESCRIPTION: SEQ ID NO:2:

```
GCAGACACTC TATGCCTGTG TGG                                                      23

(2) INFORMATION FOR SEQ ID NO:3:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: no (xi) SEQUENCE DESCRIPTION: SEQ ID NO:3:

AGGTGGCCTT TGACACCTAC CAGG                                                     24

(2) INFORMATION FOR SEQ ID NO:4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: no (xi) SEQUENCE DESCRIPTION: SEQ ID NO:4:

TCTGTTGTGT TTCCTCCCTG TTGG                                                     24
```

TRANSGENIC MOUSE MODEL OF PROSTATE CANCER

The U.S. Government has certain rights in the disclosed invention by virtue of grant RO1-DK37960 from the National Institutes of Health.

BACKGROUND OF THE INVENTION

The invention is generally in the field of transgenic animals and more specifically in the field of transgenic animal models of prostate cancer.

The prostate is derived from the urogenital sinus. Cross sections through this tubuloalveolar gland reveal a simple cuboidal or columnar epithelium, with no apparent differences between the cells lining its ducts and those lining its acini (reviewed in Lepor and Lawson, eds., "Prostatic Diseases" (W. B. Saunders Company, Philadelphia, 1993). The epithelium contains three cell types. Secretory luminal cells are the predominant cell type. Neuroendocrine cells are scattered between luminal cells. Basal cells lie between luminal cells and the basement membrane (reviewed in Lepor and Lawson (1993), and Bonkhoff, Eur. Urol. 30:201–205 (1996)).

The prostatic epithelium undergoes continuous self-renewal. However, turnover is on the order of months, so dividing cells are rarely observed unless there is tissue damage. Surprisingly little is known about the regulation of proliferation and differentiation in the normal mouse or human prostate. Basal cells comprise greater than 70% of the proliferating cell population in the normal adult prostate. Intermediate cell types that share features of more than one of the three lineages have been identified in normal and in neoplastic prostatic epithelium. This has led to speculation that the three lineages are interrelated and possibly derived from a common progenitor (Bonkhoff and Remberger, Prostate 28:98–106 (1996); Bonkhoff (1996)). There is some indirect evidence that this progenitor may reside within the basal cell population (reviewed in Bonkhoff (1996)).

After puberty, the prostatic epithelium requires androgens for maintenance of its proliferation and for prevention of cell death (Isaacs et al., Seminars in Cancer Biol. 5:391–400 (1994)). If the normal prostate is deprived of androgens after puberty, it will involute. The prostate never completes its morphogenesis in dogs or rats if they are castrated before sexual maturity. If these animals are supplied with testosterone later in life, the prostate can complete its maturation— suggesting the existence of a stem cell that does not depend upon androgens for its survival (reviewed in Lepor and Lawson (1993)).

Adenocarcinoma of the prostate is the most frequently diagnosed cancer in men in the United States, and is the second leading cause of male cancer deaths (Karp et al., Cancer Res. 56:5547–5556 (1996)). The exquisite susceptibility of this organ to cancer in humans is not understood. Skenes glands represent the female homolog of the prostate but are not a site where neoplastic transformation is observed.

Increasing numbers of patients with occult prostate cancer are being identified by a rapid, sensitive screening assay for prostate specific antigen (PSA). Large scale PSA screening has produced a dilemma, since most patients with carcinoma in situ will die of other causes before suffering symptoms of their cancer. Those individuals whose disease will progress rapidly may be saved if they are treated early. However, these individuals are not easily distinguished from those who will only have indolent disease (Lepor and Lawson (1993), and Karp et al. (1996)). A better understanding of the molecular mechanisms leading to malignant transformation of the prostate is needed to explain its high prevalence, and to assist in the identification of those patients who are at risk for aggressive disease and who, therefore, would benefit from aggressive therapy.

Surgical or chemical androgen ablation is often used to treat patients when their adenocarcinoma is no longer confined to the prostate. This approach is effective initially in 60 to 80% of patients. However, the cancers inevitably become androgen-independent (reviewed in Lepor and Lawson (1993)). This may be due to selection of a small number of possibly pre-existing androgen-independent cells, or to conversion of androgen-dependent cells to an androgen-independent state (Isaacs and Coffey, Cancer Res. 41:5070–5075 (1981); Rennie et al., J. Steroid Biochem. Mol. Biol. 37:843–847 (1990)). Mutations in the androgen receptor have been identified in some androgen-independent human prostatic tumors. However, the presence or absence of the androgen receptor does not correlate with the androgen-dependence of prostatic cancers in the same the way that the presence or absence of estrogen and progesterone receptors correlate with the hormone-dependence of breast cancers (reviewed in Sluyser, Crit. Rev. Onc. 5:539–554 (1994)). Therefore, it is difficult to predict whether an individual patient will respond to androgen ablation therapy. A better understanding of the evolution of androgen resistance is important for the development of better treatment strategies for human prostate cancer.

Several observations suggest that the anti-apoptotic regulator Bcl-2 plays a role in development of androgen-independence. Bcl-2 is normally expressed in basal cells, which do not show the same apoptotic response to androgen withdrawal as luminal cells (Rouleau et al., Mol. Endocrinol. 4:2003–2013 (1990)). Prostate cancer cells expressing Bcl-2 in vitro and in vivo are also resistant to androgen withdrawal (Raffo et al., Cancer Res. 55:4438–4445 (1995)). Colombel et al., Am. J. Path. 143:390–400 (1993), conducted a retrospective study of human prostatic adenocarcinomas. They included primary lesions as well as metastatic foci in their survey. Their analysis indicated that all androgen-independent tumors from patients with hormone-refractory disease produce Bcl-2. In contrast, only a subset of androgen-dependent tumors contained detectable levels of Bcl-2. Similar results were obtained in a separate study (McDonnell et al., Cancer Res. 52:6940–6944 (1992)). Based on these results, Colombel and coworkers hypothesized that Bcl-2 expression might enable prostatic cancer cells to survive in an androgen-deprived environment and confer resistance to androgen withdrawal therapies. This hypothesis needs to be tested in a genetically well defined model of human prostatic cancer.

Fifty to seventy five percent of prostatic adenocarcinomas show some neuroendocrine differentiation, as defined by immunohistochemical stains for markers such as chromogranin A. Although the significance of this phenotype is controversial, some data indicate that neuroendocrine differentiation correlates with a hormone refractory state and a poor long term prognosis (reviewed in Logothetis and Hoosein, "Comprehensive Textbook of Genitourinary Oncology" (Williams & Wilkins, Baltimore, 1996); di Sant'Agnese and Cockett, Cancer 78:357–361 (1996)). Two studies have demonstrated expression of Bcl-2 in prostatic secretary (luminal) cells that are in contact with neuroendocrine cells (Cohen et al., Pathology 27:229–232 (1995); Segal et al., Arch. Pathol. Lab Med. 118:616–618 (1994)). Bcl-2 is not normally detected in luminal cells. These observations have led to the notion that signalling between neuroendocrine cells and luminal cells results in induction of Bcl-2 in luminal cells. Since the presence of neuroendocrine cells in adenocarcinoma may correlate with an androgen-independent state, it is possible that this induction of Bcl-2 expression by neuroendocrine cells may be related to development of androgen-independence.

Finally, prostatic intraepithelial neoplasia (PIN) is generally believed to be a precursor to adenocarcinoma of the prostate although formal proof is lacking. A genetically well-defined and manipulatable model is needed that can be used to dissect the molecular events associated with development of, and progression from, PIN.

Three transgenic models of prostate cancer have been reported in the literature. Each model has used different transcriptional regulatory elements to drive expression of simian virus 40 large T antigen (TAg).

The human fetal Gγ globin promoter was used to express TAg in erythroid cells (Perez-Stable et al., *Lab Invest.* 74:363–373 (1996); Perez-Stable et al., *Cancer Res.* 57:900–906 (1997)). In one Gγ-TAg pedigree, males developed prostate tumors that showed "mixed neuroendocrine and epithelial cell features". Females developed adrenocortical tumors. Prostatic neoplasia appeared relatively late. PIN was observed in only a subset of transgenic males by 4 to 5 months of age. However, by 6 months, 90% of hemizygous males had palpable tumor masses. Tumors were said to visibly "metastasize" to lymph nodes, adrenal glands, and the kidney but the issue of metastastic spread is confounded by the fact that the transgene is expressed in some of these organs in this and other pedigrees. This model is the only one of the three published models of prostatic cancer in which neuroendocrine differentiation is reported. Several neuroendocrine cell markers were detected by Western blot but the presence of secretory granules in tumor cells could not be confirmed by EM. Based on these findings, the authors postulated that TAg was expressed in a luminal epithelial cell with neuroendocrine features. When castration was performed after puberty, tumor development was unaffected, suggesting androgen-independence. The fact that prostatic cancer was only seen in one of several lines of Gγ-TAg transgenic mice suggests an insertion site effect.

Maroulakou et al., *Proc. Natl. Acad. Sci. USA* 91:11236–11240 (1994) and Shibata et al., *Cancer Res.* 56:4894–4903 (1996) reported that several pedigrees of mice expressing TAg under the control of the rat prostatic steroid binding protein promoter develop incompletely penetrant prostate tumors. TAg is initially expressed in "scattered apparently normal-appearing prostate epithelial cells" (Maroulakou et al. (1994)). PIN does not appear in some animals until 8 months of age. Prostate tumors often do not develop for 6 to 8 months and are not metastatic. The authors do not describe any experiments that tested the androgen-sensitivity of these lesions. Furthermore, these mice have significant health problems due to transgene expression at other sites: that is, bone, cartilage, thyroid, salivary glands and the nasal epithelium.

The rat probasin gene (rPB) encodes an androgen- and zinc-regulated protein that is only expressed in the dorsolateral prostatic epithelium. Greenberg et al. *Proc. Natl. Acad. Sci. USA* 92:3439–3443 (1995) and Gingrich et al., *Cancer Res.* 56:4096–4102 (1996) found that nucleotides −426 to +28 of rPB could be used to express foreign gene products to this cell population in transgenic mice. Probasin-TAg transgenic mice develop androgen-dependent prostate cancer. However, there is significant variability in the rate of tumor development between transgenic lines, attributed to varying levels of TAg. For example, members of one high-expressing pedigree develop large, multinodular tumors by 10 weeks of age, whereas members of another, low-expressing pedigree show only profound hyperplasia at 33 weeks. Expression of TAg is directed to mature luminal epithelial cells, where the presence of the oncoprotein precedes transformation (PIN). The authors noted that "positively staining nuclei were plentiful in epithelial cells lining some of the nontumoral glands, and interestingly, most of the TAg-positive nuclei were indistinguishable from their unstained neighbors" (Gingrich et al. (1996)). Metastases occur in this model.

Accordingly, it would be useful to have an animal model of prostate cancer that provides a consistent phenotype, where neoplasia progresses more rapidly, and produces hormone refractory tumors.

Therefore, it is an object of the present invention to provide a transgenic animal model of prostate cancer.

It is another object of the present invention to provide a method of testing compounds for an effect on initiation, progression, or both, of prostate tumors.

BRIEF SUMMARY OF THE INVENTION

Disclosed are transgenic animals that produce prostate tumors and faithfully recapitulate many of the features of human prostatic carcinoma. It has been discovered that transcriptional regulatory elements active in Paneth cells, granule goblet cells, intermediate cells, or a combination, when used to express Simian Virus 40 large T antigen (TAg) in a transgenic animal leads to development of prostate tumors in the animals. The transcriptional regulatory elements used are derived from the cryptdin-2 (CR2) gene. The disclosed animals develop prostatic intraepithelial neoplasia (PIN) at an early age. Progression with local invasion, loss of androgen-dependence and eventual metastases are hallmarks of the disclosed transgenic animals. Preferred embodiments of the disclosed transgenic animals have several important characteristics:

(1) The disease is fully penetrant—all animals expressing the transgene develop prostate cancer.
(2) The first appearance of SV40 TAg always coincides with the appearance of cellular atypia in prostatic acini, suggesting immediate initiation of neoplasia.
(3) The rate of progression of the neoplasia is rapid.
(4) Prostatic adenocarcinomas in the transgenic animals exhibit foci of neuroendocrine differentiation which, in human prostatic carcinomas, has been correlated with a hormone refractory state and a poor long term prognosis.
(5) Metastatic lesions are common in the lymph nodes, liver, lung, and bone of the disclosed transgenic animals and are evident early in life.
(6) The lifespan of the disclosed transgenic animals is not shortened by transgene-related pathology in other organs. Female transgenic animals develop normally and have a normal lifespan.

DETAILED DESCRIPTION OF THE INVENTION

Disclosed are transgenic animals that produce prostate tumors and faithfully recapitulate many of the features of human prostatic carcinoma. It has been discovered that transcriptional regulatory elements active in Paneth cells, granule goblet cells, intermediate cells, or a combination, when used to express Simian Virus 40 large T antigen (TAg) in a transgenic animal leads to development of prostate tumors in the animals. The transcriptional regulatory elements used are derived from the cryptdin-2 (CR2) gene. The disclosed animals develop prostatic intraepithelial neoplasia (PIN) at an early age. Progression with local invasion, loss of androgen-dependence and eventual metastases are hallmarks of the disclosed transgenic animals. Preferred embodiments of the disclosed transgenic animals have several important characteristics:

(1) The disease is fully penetrant—all animals containing the SV40 TAg transgene develop prostatic cancer.

(2) The first appearance of SV40 TAg always coincides with the appearance of cellular atypia in prostatic acini, suggesting immediate initiation of neoplasia.

(3) The rate of progression of the neoplasia is rapid.

(4) Prostatic adenocarcinomas in the transgenic animals exhibit foci of neuroendocrine differentiation which, in human prostatic carcinomas, has been correlated with a hormone refractory state and a poor long term prognosis.

(5) Metastatic lesions are common in the lymph nodes, liver, lung, and bone of the disclosed transgenic animals and are evident early in life.

(6) The lifespan of the disclosed transgenic animals is not shortened by transgene-related pathology in other organs. Female transgenic animals develop normally and have a normal lifespan.

An example of the disclosed transgenic animals was originally created to study the function of Paneth cells, one of four epithelial cell lineages derived from the small intestine's multipotent stem cell (Cheng and LeBlond, *Am. J. Anat.* 141:537–562 (1974); Loeffler et al., *J. Theor. Biol.* 160:471–491 (1993)). Paneth cells secrete antimicrobial peptides and growth factors. They are positioned at the base of crypts of Lieberkuhn, just below the stem cell zone (Bjerknes and Cheng, *Am. J. Anat.* 160:51–63 (1981) and Bjerknes and Cheng, *Am. J. Anat.* 160:65–75 (1981)). Two types of lineage ablation experiments were performed to investigate the role of Paneth cells in establishing and maintaining the crypt's stem cell niche and in modulating host-microbial interactions in the small intestine (one of which is described in the examples). At the time these experiments were designed, it was believed that nucleotides −6500 to +34 of the mouse cryptdin-2 gene (CR2) was only expressed in Paneth cells (Bry et al., *Proc. Natl. Acad. Sci. USA* 91:10335–10339 (1994)). Therefore, CR2 was used to direct expression of either TAg or an attenuated form of diphtheria toxin A fragment (tox176; Maxwell et al., *Mol. Cell. Biol.* 7:1576–1579 (1987)) to members of this lineage (CR2-TAg or CR2-tox176 mice). Mature Paneth cells were ablated in both CR2-TAg and CR2-tox176 animals. TAg expression also produced an expansion of a bi-potential crypt progenitor cell that apparently gives rise to both Paneth and goblet cell lineages. The loss of mature Paneth cell and the modest expansion of the bi-potential progenitor had no detectable effects on (a) intestinal development; (b) differentiation or migration of absorptive enterocytes; (iii) the organization and composition of gut-associated lymphoid tissue (GALT); or (iv) the crypt-villus and duodenal-colonic distribution of components of the normal intestinal microflora. None of the 100 male or female CR2-TAg mice surveyed develop intestinal neoplasms.

At six weeks of age, TAg-positive cells appear in small clusters located within a few acini scattered throughout the prostate of CR2-TAg mice. The clusters are located underneath a layer of normal, TAg-negative luminal epithelial cells and above the basement membrane: that is, in the area normally occupied by basal cells. The TAg-positive cells appear more round than basal cells, and cause the clusters to produce irregular thickening of the acinar epithelium. Double-label immunohistochemistry revealed that high molecular weight cytokeratin (a marker of basal cells) was not detectable in these TAg-positive cells. Moreover, cells immediately underlying or overlying the clusters do not stain for this marker.

It is possible that the CR2 promoter supports expression of foreign gene products in a very minor subpopulation of prostatic cells that can only be identified if they are amplified (for example, as they are in CR2-TAg mice). Alternatively, the CR2-TAg transgene may contain a novel combination of cis-acting transcriptional regulatory elements that allow activation of expression in a subset of the basal cell population.

Without wishing to be limited to any particular mechanism, it is believed that initial expression of TAg in prostatic basal cells from promoters (such as transcriptional regulatory elements of the cryptdin gene) leads to a series of events that rapidly converts them into a highly proliferative, malignant population. The fate of these initiated cells contrasts with the fate of TAg-expressing Paneth cell progenitors in the same animals. These progenitors show no signs of neoplastic transformation.

Characteristics of CR2-TAg Mice

Many cancers contain several clonal populations (Ohmura and Hattori, *J. Cancer Res. & Clin. Onc.* 121:321–326 (1995); Pandis et al., *Cancer* 76:250–258 (1995); Bjerknes et al., *Cancer Res.* 57:355–361 (1997); Ferraris et al., *Hum. Genet.* 99:202–205 (1997)). PIN in humans is multifocal. The multifocal nature of PIN, even at its earliest stages of presentation, raises the possibility that prostatic adenocarcinoma arises at multiple sites (Bostwick, *Hum. Pathol.* 23:242–248 (1992)).

Transgene expression and PIN both occur in multiple, anatomically distinct sites (acini), in CR2-TAg mice. Initiation of transgene expression in the basal cell region of CR2-TAg acini coincides with the initiation of PIN. All cells in each focus in PIN within a given acinus appear to be TAg-positive, raising the question of whether each focus represents the clonal descendants of a single initiated cell.

Between two and four months of age, the neoplastic population of cells in initiated CR2-TAg acini expands. At the same time, the number of acini exhibiting PIN appears to increase. The apparent expansion of the number of acini with PIN raises the question of whether expansion occurs in an "acinus-autonomous" fashion or whether pre-existing acini with PIN are somehow able to recruit adjacent normal acini through elaboration of trophic factors. Understanding the answer to this question may provide important insights about the factors in humans that promote aggressive as opposed to indolent prostatic neoplasia.

PIN progresses in CR2-TAg mice with the development of large solid masses (sheets) of neoplastic cells that are very poorly differentiated. Immunohistochemical studies of these more advanced lesions have shown that expression of TAg is heterogeneous: many malignant cells in a given focus do not stain positively for the oncoprotein. This finding may be very important. On the one hand, it may indicate that tumor progression involves acquisition of other genetic lesions that eventually obviate the need for transgene expression. In support of this theory, Ewald et al., *Science* 273:1384–1386

(1996), demonstrated that transient expression of TAg in salivary glands is sufficient to induce tumors and that these tumors are able to progress even after expression of TAg is shut off. It is also possible that at some point in the evolution of the prostatic neoplasia, TAg-positive cells can establish collaborative interactions with TAg-negative cells so that these "normal" TAg-negative cells are themselves initiated and recruited into a "polyclonal tumor".

The juxtaposition of normal and neoplastic acini within the prostate of a single CR2-TAg mouse provides an opportunity to compare and contrast expression of a variety of gene products that may contribute to the evolution of neoplasia. In essence, at this stage of the evolution of tumorigenesis, each mouse may carry an internal control: normal acini without PIN. Based on this, the patterns of accumulation of a variety of molecules that may regulate initiation, progression, or both, can be surveyed. For example, immunohistochemical studies disclosed that expression of a variety of integrins subunits ($\alpha$1,3,4,6 and $\beta$1,4,7) is silenced in TAg-positive cells at very early stages of PIN and remains suppressed throughout the evolution of this cancer.

By four months of age, cribriform glandular structures are seen in CR2-TAg prostates, along with extensive invasion into the surrounding stroma. By six months, the majority of prostate tumors are large, solid masses of cells with little remaining architecture. As noted above, the tumors show light microscopic features of neuroendocrine differentiation (rosette formation; palisading). The presence of neuroendocrine secretory granules in tumor cells has been confirmed by electron microscopy.

Between four and six months, adenocarcinomas aggressively metastasize in greater than 85% of CR2-TAg males. Metastases have been found in lymph nodes and bone, the two most common sites of metastasis in human adenocarcinoma. Liver and lung are also affected. Death of CR2-TAg transgenic mice occurs between six and seven months and appears to be due to complications of metastases and/or to acute kidney failure from the tumor's obstruction of the bladder outlet.

Immunohistochemical surveys have shown that CR2-TAg mice with PIN express androgen receptors in their initiated, TAg-positive cells. To examine the issue of androgen dependence in the evolution of this model of prostatic adenocarcinoma, CR2-TAg male mice were castrated at postnatal day 21 (that is, prior to sexual maturity). No prostatic tissue is evident in castrated mice at two to three months of age. At four months of age, prostatic tumors in castrated mice were noticeably smaller than in non-castrated CR2-TAg cagemates. This difference in tumor size diminishes by six months. Metastatic disease is evident in both groups of animals at six months. There are no appreciable differences in the distribution of metastases at this time point.

These findings suggest initial androgen-dependence and subsequent escape to androgen-resistance—features that are the hallmark of human prostatic cancers. These findings also imply that TAg is expressed by a cell type that can survive past puberty without androgens. Thus, it is believed that the disclosed transgenic animals will be useful for defining the roles of testosterone and dihydrotestosterone in the progression of prostatic malignancy.

Production of Transgenic Animals

Construction of transgenes can be accomplished using any suitable genetic engineering technique, such as those described in Sambrook et al., *Molecular Cloning: A Laboratory Manual* (Cold Spring Harbor Laboratory, N.Y., (1989)). Many techniques of transgene construction and of expression constructs for transfection or transformation in general are known and may be used for the disclosed constructs. An example of the construction of a preferred TAg transgene construct is described in the example. Although the use of the SV40 large T antigen in the disclosed transgene constructs is preferred, other proteins, encoded by oncogenes, which have similar effects when properly expressed in basal cell region prostatic tissue can also be used. Such proteins are referred to herein as oncogene proteins.

Any promoter that promotes expression of TAg in developing prostate cells in the basal cell region can be used in the disclosed constructs. A preferred promoter is the promoter of the cryptdin-2 gene, and in particular the region of the cryptdin-2 gene from −6500 to +34. A TAg transgene construct using the cryptdin-2 promoter is described in the example. As used herein, the term promoter is intended to encompass transcriptional regulatory elements, that is, all of the elements that promote or regulate transcription, including core elements required for basic interaction of RNA polymerase and transcription factors, upstream elements, enhancers, and response elements (Lewin, "Genes V" (Oxford University Press, Oxford) pages 847–873). Reference herein to the transcriptional regulatory elements of a gene or class of gene includes both all or an intact region of the naturally occurring transcriptional regulatory elements and modified forms of the transcriptional regulatory elements of the gene or group of genes. Such modified forms include rearrangements of the elements, deletions of some elements or extraneous sequences, and insertion of heterologous elements. The modular nature of transcriptional regulatory elements and the absence of position-dependence of the function of some regulatory elements such as enhancers makes such modifications possible. Numerous techniques are available for dissecting the regulatory elements of genes to determine their location and function. Such information can be used to direct modification of the elements, if desired. It is preferred, however, that an intact region of the transcriptional regulatory elements of a gene be used.

A. Animal Sources

Animals suitable for transgenic experiments can be obtained from standard commercial sources such as Taconic (Germantown, N.Y.). Many strains are suitable, but Swiss Webster (Taconic) female mice are preferred for embryo retrieval and transfer. B6D2F$_1$ (Taconic) males can be used for mating and vasectomized Swiss Webster studs can be used to stimulate pseudopregnancy. Vasectomized mice and rats can be obtained from the supplier.

B. Microinjection Procedures

Any suitable technique for introduction of a transgene construct into embryonic cells can be used. For example, DNA clones for microinjection can be cleaved with enzymes appropriate for removing the bacterial plasmid sequences and the DNA fragments electrophoresed on 1 % agarose gels in TBE buffer (Sambrook et al. (1989)). The DNA bands can be visualized by staining with ethidium bromide, and the band containing the desired DNA sequences is excised. The excised band can then placed in dialysis bags containing 0.3M sodium acetate, pH 7.0. DNA can be electroeluted into the dialysis bags, extracted with phenol-chloroform (1:1), and precipitated by two volumes of ethanol. The DNA can be redissolved in 1 ml of low salt buffer (0.2M NaCl, 20 mM Tris, pH 7.4, and 1 mM EDTA) and purified on an Elutip-D™ column. The column should first be primed with 3 ml of high salt buffer (1M NaCl, 20 mM Tris, pH 7.4, and 1 mM EDTA) followed by washing with 5 ml of low salt buffer. The DNA solutions can be passed through the column for three times to bind DNA to the column matrix. After one wash with 3 ml of low salt buffer, the DNA can be eluted with 0.4 ml of high salt buffer and precipitated by two volumes of ethanol. DNA concentrations can be measured by absorption at 260 nm in a UV spectrophotometer. For microinjection, DNA concentrations can be adjusted to 5 $\mu$g/ml in 5 mM Tris, pH 7.4 and 0.1 mM EDTA. Other methods for purification of DNA for microinjection are also described in Hogan et al., *Manipulating the Mouse Embryo* (Cold Spring Harbor Laboratory, Cold Spring Harbor, N.Y., (1986)); in Palmiter et al., *Nature* 300:611 (1982); in *The Qiagenologist, Application Protocols*, 3rd edition, published by Qiagen, Inc., Chatsworth, Calif.; and in Sambrook et al., *Molecular Cloning: A Laboratory Manual* (Cold Spring Harbor Laboratory, Cold Spring Harbor, N.Y., 1989). The procedures for manipulation of the rodent embryo and for microinjection of DNA are described in detail in Hogan et al., *Manipulating the Mouse Embryo* (Cold Spring Harbor Laboratory, Cold Spring Harbor, N.Y., (1986)), the teachings of which are incorporated herein.

C. Transgenic Mice

The following is a preferred means of producing transgenic mice. Female mice six weeks of age are induced to superovulate with a 5 IU injection (0.1 cc, ip) of pregnant mare serum gonadotropin (PMSG; Sigma) followed 48 hours later by a 5 IU injection (0.1 cc, ip) of human chorionic gonadotropin (hCG; Sigma). Females are placed with males immediately after hCG injection. Twenty-one hours after hCG injection, the mated females are sacrificed by $CO_2$ asphyxiation or cervical dislocation and embryos are recovered from excised oviducts and placed in Dulbecco's phosphate buffered saline with 0.5% bovine serum albumin (BSA; Sigma). Surrounding cumulus cells are removed with hyaluronidase (1 mg/ml). Pronuclear embryos are then washed and placed in Earle's balanced salt solution containing 0.5% BSA (EBSS) in a 37.5° C. incubator with a humidified atmosphere at 5% $CO_2$, 95% air until the time of injection. Embryos can be implanted at the two cell stage.

Randomly cycling adult female mice are paired with vasectomized males. Swiss Webster or other comparable strains can be used for this purpose. Recipient females are mated at the same time as donor females. At the time of embryo transfer, the recipient females are anesthetized with an intraperitoneal injection of 0.015 ml of 2.5% avertin per gram of body weight. The oviducts are exposed by a single midline dorsal incision. An incision is then made through the body wall directly over the oviduct. The ovarian bursa is then torn with watchmakers forceps. Embryos to be transferred are placed in DPBS (Dulbecco's phosphate buffered saline) and in the tip of a transfer pipet (about 10 to 12 embryos). The pipet tip is inserted into the infundibulum and the embryos transferred. After the transfer, the incision is closed by two sutures.

D. Transgenic Rats

The preferred procedure for generating transgenic rats is similar to that of mice (Hammer et al., *Cell* 63:1099–112 (1990)). Thirty day-old female rats are given a subcutaneous injection of 20 IU of PMSG (0.1 cc) and 48 hours later each female placed with a proven male. At the same time, 40–80 day old females are placed in cages with vasectomized males. These will provide the foster mothers for embryo transfer. The next morning females are checked for vaginal plugs. Females who have mated with vasectomized males are held aside until the time of transfer. Donor females that have mated are sacrificed ($CO_2$ asphyxiation) and their oviducts removed, placed in DPBS (Dulbecco's phosphate buffered saline) with 0.5% BSA and the embryos collected. Cumulus cells surrounding the embryos are removed with hyaluronidase (1 mg/ml). The embryos are then washed and placed in EBSS (Earle's balanced salt solution) containing 0.5% BSA in a 37.5° C. incubator until the time of microinjection.

Once the embryos are injected, the live embryos are moved to DPBS for transfer into foster mothers. The foster mothers are anesthetized with ketamine (40 mg/kg, ip) and xylazine (5 mg/kg, ip). A dorsal midline incision is made through the skin and the ovary and oviduct are exposed by an incision through the muscle layer directly over the ovary. The ovarian bursa is torn, the embryos are picked up into the transfer pipet, and the tip of the transfer pipet is inserted into the infundibulum. Approximately 10 to 12 embryos are transferred into each rat oviduct through the infundibulum. The incision is then closed with sutures, and the foster mothers are housed singly.

An example of the production of the disclosed transgenic animals is described in the examples.

Methods

The disclosed transgenic animals can be used as research tool to determine genetic and physiological features of prostate cancer, and for identifying compounds that can affect prostate tumors.

In general, the method of testing compounds for an effect on prostate tumors involves (a) administering the compound to be tested to a transgenic animal as disclosed, and (b) comparing one or more characteristics of the prostate tumors in the transgenic animal to which the compound was administered with the same characteristics of the prostate tumors in the transgenic animal to which the compound has not been administered. Differences in one or more of the one or more characteristics indicates that the compound has an effect on prostate tumors.

In general, the method of identifying markers associated with prostate tumors involves comparing the presence, absence, or level of expression of genes in prostatic tissue from a transgenic animal as disclosed and prostatic tissue from a matching non-transgenic animal. Differences between the animals in the presence, absence, or level of expression of a gene indicates that the expression of the gene is a marker associated with prostate tumors.

Effects of Androgen Inhibition on Prostate Cancer

The disclosed transgenic animals can also be used to conduct genetic-pharmacologic tests of the effect of inhibition of androgen production on initiation, progression, or both of prostatic cancer. For example, steroid 5-$\alpha$ reductase converts testosterone to dihydrotestosterone. There are two 5-$\alpha$ reductase isozymes, encoded by separate genes -Srd5$\alpha$1 and Srd5$\alpha$2. Inhibitors of both 5-$\alpha$ reductase isozymes, can be used to treat the disclosed transgenic animals beginning at sexual maturity. This tests whether the inhibitors will prevent or slow development of PIN, adenocarcinoma, or metastasis and lead to prolonged survival relative to controls treated with vehicle alone. Castrated animals can be included as a positive control.

Both testosterone and dihydrotestosterone bind to the androgen receptor, but with different affinities and different effects in different tissues (reviewed in Randall, *Bailliere's Clin. Endo. Metabol.* 8:405–431 (1994)). Although dihydrotestosterone appears to be the major effector of prostatic differentiation and homeostasis, there is some evidence that testosterone can also fill this role if present in high concentrations (Homma et al., *J. Natl. Cancer Inst.* 89:803–807 (1997)).

The effects of androgens on initiation, progression, and apoptosis can be tested in a number of ways. The following techniques are described in terms of transgenic mice but can be adapted for use with any of the disclosed transgenic animals.

(a) An inhibitor of one or both steroid 5-αreductase isozymes, can be administered to CR2-TAg mice by gavage or other methods, beginning at postnatal day 28 (P28). The effects on initiation and progression can be monitored by performing blinded histopathologic studies of the prostates of untreated CR2-TAg animals, treated CR2-TAg mice, and untreated control castrated (at P21) CR2-TAg mice. Animals from each group can be sacrificed at four time points: 10 weeks, 4 months, 6 months, and terminal. Circulating drug, testosterone, and dihydrotestosterone levels can be measured at the time of sacrifice. Hematoxylin and eosin-stained sections can be histopathologically scored and androgen receptor expression can be examined by immunohistochemistry. This assay tests whether the 5-αreductase inhibitor will prevent or slow development of PIN, adenocarcinoma and/or metastasis and lead to prolonged survival relative to controls treated with vehicle alone.

(b) Castration of CR2-TAg mice has already been performed on postnatal day 21 (that is, prior to sexual maturity) and the effects on tumor initiation and progression defined. Castrations can also be performed at various times after initiation of tumorigenesis and the effects on progression can be determined. Progression within individual animals can be monitored by PET scanning using fluorine-18-labeled androgen receptor ligands and fluorine-18-labeled deoxyglucose.

Positron Emission Tomography (PET) has been successfully performed on mice (McCarthy et al., *J. Chem. Ed.* 71:830–836 (1994)). $^{18}$F-androgen receptor ligands have also been developed for PET scanning of humans with prostatic cancer (for example, 16β-[$^{18}$F]fluoro-5α-dihydrotestosterone; see Bonasera et al., *J. Nuclear Med.* 37:1009–1015 (1996)). Tumors as small as 4 mm can be resolved in humans with this technique (NB by six months of age, prostatic tumors in the disclosed CR2-TAg mice are several centimeters in diameter). PET scanning with these ligands as well as [$^{18}$F]fluoro-deoxyglucose (FDG) should allow monitoring of tumor growth and metastatic spread over time in individual CR2-TAg mice. Thus, PET can be used as one parameter to assess the effects of androgen ablation on disease progression.

Testosterone is produced by the adrenal glands as well as the testes, so complete hormone withdrawal is not assured with castration. For example, the following additional genetic tests can be performed using the disclosed transgenic animals.

(c) Tfm (testicularly feminized) mice carry a naturally occurring null mutation in the X-linked androgen receptor gene (He et al., *Nucleic Acids Res.* 19:2373–2378 (1991), Gaspar et. al., *Proc. Natl. Acad. Sci.* USA 88:8606–8610 (1991)). Males hemizygous for this mutation ($AR^{Tfm}/Y$) have external genitalia that appear female. Hence, the heterogametic sex must be identified by screening "female" mice by PCR for the presence of a Y-linked gene such as SRY. Male CR2-TAg transgenic mice can be crossed to females heterozygous for $AR^{Tfm}$. The resulting $AR^{Tfm}/Y$, TAg offspring can be examined for tumor formation at six months of age. These animals should be incapable of responding to either testosterone or dihydrotestosterone signaling from conception. $AR^+/Y$, CR2-TAg animals derived from these crosses can serve as reference controls. This is a powerful genetic test for determining whether the cell population in which TAg is expressed and tumorigenesis initiated is androgen-dependent or androgen-independent.

Identification of Prostate Cancer Markers

The disclosed transgenic animals can also be used to identify molecular markers that (i) can be used to predict whether patients with carcinoma in situ will have indolent or aggressive disease, and (ii) may be mediators of progression. Identification of such mediators would be useful since they are possible therapeutic targets. Identification of markers can take several forms.

Directed screens. The juxtaposition of normal and neoplastic acini within the prostate of the disclosed animals allows comparison of a variety of gene products in normal and neoplastic acini. For example, patterns of accumulation of a variety of molecules that may regulate growth can be surveyed using immunohistochemical methods. Screens directed at analyzing expression of specific genes or groups of molecules implicated in pathogenesis can be continued during the life of the transgenic animal. Expression can be monitored by immunohistochemistry as well as by protein and RNA blotting techniques. Metastatic foci, once formed, can also be subjected to such comparative surveys.

Genomic screens. Prostatic tissue can be recovered from young transgenic animals (predominant histopathologic change=PIN with androgen-dependency) and older transgenic animals (advanced androgen-independent adenocarcinoma), and compared with similar material recovered from age-matched normal littermate controls to catalog genes that are induced or repressed as disease is initiated, and as disease progresses to its final stages. These surveys will generally include cellular populations in the prostate. However, the lectin panning described below could allow genomic screens to be conducted on selected 'initiated' cell populations, or populations selected at various points during progression (including metastases).

This analysis can also be extended to include an assessment of the effects of various treatment paradigms (including the use of compounds identified as affecting prostate tumors in the transgenic animals) on differential gene expression (DGE). The information derived from the surveys of DGE can ultimately be correlated with disease initiation and progression in the transgenic animals.

Identifying the Source of Initiation of Tumorigenesis

Initiation of tumorigenesis may be limited to single cells and their clonal descendants or may occur in the basal cell lineage. The disclosed transgenic animals can be used to identify the source.

(a) To determine the source of tumorigenesis, lineage-specific markers can be developed for prostate tissue. In general, a panel of lectin and antibodies can be developed that recognize markers of the three epithelial lineages in the normal adult prostate. Glycoconjugate production can be a very sensitive indicator of cellular proliferation and differentiation programs. This can be accomplished using techniques that have been used for other tissues such as intestinal tissue where a panel of more than 40 lectins have been used to describe epithelial differentiation in the intestine of FVB/N mice. Sections of prostate tissue obtained from normal animals can be stained with each of the lectins. The cellular patterns of expression of (i) regulators of the G1/S transition (for example, cyclins D1, E; cdks 2 and 4); (ii) regulators of apoptosis (Bcl-2, Bcl-x, Bak, p53); (iii) mediators of cell-cell and cell substratum adhesion and signaling (for example, E-cadherin, β-catenin, Apc, ZO-1, integrins); and (iv) members of the cryptdin family and other "Paneth cell" products can also be surveyed to determine lineage-specific expression. These single and multilabel immunohistochemical surveys can be performed using techniques similar to those used for the intestine (such as those described in the example). Sensitive detection schemes (that is, tyramide signal amplification) can also be used.

(b) The markers identified in (a) can then be used in conjunction with antibodies to TAg to characterize the cell type that initially expresses TAg in the disclosed transgenic animals. Young animals will contain acini with PIN at various stages of evolution. Some acini will only have a single small cluster of TAg-positive cells and therefore provide an example of "early initiation". Other acini in the same animal will have more advanced PIN. The morphologic features of TAg-positive cells present at these various stages of PIN can be defined by EM immunohistochemistry, using methods such as those described in the example. Light and EM immunohistochemical techniques can also be used to survey TAg expression at earlier stages of prostate development.

(c) Using the identified lectin markers to specifically mark initiated cell populations in foci of PIN, these cells can be recovered by lectin panning. Cellular suspensions can be prepared from young transgenic animals for this purpose. The purity of the lectin-selected population can be assessed by surveying TAg expression with immunohistochemistry. The recovery of an initiated population will allow analysis of global changes in gene expression at early stages in the evolution of this disease (see discussion above).

(d) The disclosed transgenic animals can also be used to determine whether TAg expression is necessary for initiation, whether sustained expression of TAg is required for progression, and whether collaborative interactions between TAg-expressing and -nonexpressing cells occur during the course of tumorigenesis.

As noted above, PIN is multifocal. TAg immunohistochemistry has shown that cells within a given focus of PIN appear monophenotypic with respect to TAg expression. In more advanced lesions in older mice, TAg expression is heterogeneous: many malignant cells in a given focus do not stain positively for the oncoprotein. This change may be due to acquisition of other genetic lesions that eventually obviate the need for transgene expression during tumor progression. It may also be that at some point in the evolution of the prostatic neoplasia, TAg-positive cells establish collaborative interactions with TAg-negative cells so that these "normal" TAg-negative cells are themselves initiated and recruited into a "polyclonal tumor". Lineage analysis using aggregation chimeras produced from the combination of B6 morulae homozygous for ROSA26 and FVB/N morulae hemizygous CR2-TAg. Single and multilabel immunohistochemical methods performed on tissue from these chimeras will allow determination of whether prostatic tumors and their metastases have incorporated any lacZ-positive nontransgenic B6 cell populations.

EXAMPLE

The following illustrates the production and some characteristics of an example of the disclosed transgenic animals. Abbreviations used include: SV40 TAg, Simian virus 40 large T antigen; CR2, nucleotides −6500 to +34 of the mouse cryptdin-2 gene; hGH, human growth hormone; P, postnatal day; BrdU, 5-bromo-2'-deoxyuridine; PAS, periodic acid Schiff stain; EPX, endogenous peroxidases; TSA, tyramide signal amplification; HRP, horseradish peroxidase; FITC, fluorescein isothiocyanate; Cy3, indocarbocyanine; GALT, gut-associated lymphoid system.

Production of CR2-TAg Transgenic Mice

Construction of transgenes—A 2.7-kb DNA fragment containing Simian virus 40 large T antigen (SV40 TAg) was excised from pIF-TAg-hGH (Hauft et al., *J. Cell Biol.* 117:825–839 (1992)) with BamHI and subcloned into the BamHI site of pCR-H1 (Bry et al., *Proc. Natl. Acad. Sci. USA* 91:10335–10339 (1994)). This yielded pCR2-TAg which contained SV40 TAg under the control of nucleotides −6500 to +34 of the mouse cryptdin-2 gene (Huttner et al., *Genomics* 19:448–453 (1994)).

Generation of transgenic mice—A 9.2-kb fragment containing cryptdin-$2^{-6500\ to\ 34}$ and SV40 TAg (CR2-TAg) was released from pCR2-TAg by digestion with NotI and EcoRI. An 8.3-kb fragment containing cryptdin-$2^{-6500\ to\ +34}$ linked to hGH$^{+3\ to\ +2150}$ (CR2-hGH) was released from pCR-H1 with EcoRI (Bry et. al., *Proc. Natl. Acad. Sci. USA* 91:10335–10339 (1994)). Each fragment was purified by agarose gel electrophoresis followed by glass bead extraction (Geneclean, Bio 101) and used for pronuclear injection of FVB/N oocytes. Oocytes were subsequently transferred to pseudopregnant Swiss Webster females using standard techniques (Hogan et al. (eds), (Cold Spring Harbor Laboratory Press, Cold Spring Harbor, N.Y., 1986)).

Live born mice were screened for presence of transgenes by extracting tail DNA and performing PCR using primers that anneal to hGH DNA (CR2-hGH; 5'-AGGTGGCCTTTGACACCTACCAGG-3' (SEQ ID NO:3) and 5'-TCTGTTGTGTTTCCTCCCTGTTGG-3' (SEQ ID NO:4)) or SV40 TAg DNA (CR2-TAg; 5'-ATGAATGGGAGCAGTGGTG-3' (SEQ ID NO:1) and 5'-GCAGACACTCTATGCCTGTGTGG-3' (SEQ ID NO:2)). The polymerase chain reaction mixtures (final volume=25 μL) contained 50 mM KCl, 10 mM Tris (pH 8.4), 2 mM MgCl$_2$, 200 μM dNTPs, 10 μM of each primer, 0.7 unit of Taq DNA polymerase (Boehringer Mannheim), and approximately 0.5 μg genomic DNA. The following cycling conditions were used to amplify CR2-hGH DNA: denaturation, 1 minute at 94° C.; annealing, 1.5 minutes at 55° C.; and extension, 2 minutes at 72° C. for 30 cycles. For CR2-TAg, denaturation was performed at 95° C. and annealing at 58° C.

Four CR2-hGH founders were identified from 38 live born mice and ten CR2-TAg founders were identified from 87 animals. Pedigrees were established from each of the CR2-hGH founders and from eight of the CR-TAg founders. All pedigrees were maintained by crosses to normal FVB/N littermates.

Maintenance of animals—Mice were housed in microisolater cages under a strictly controlled light cycle (lights on at 0600 h and off at 1800 h) and given a standard irradiated chow diet ad libitum (Pico rodent chow 20, PMI Feeds, St. Louis, Mo.). Routine screens for Hepatitis, Minute, Lymphocytic Choriomeningitis, Ectromelia, Polyoma, Sendai, Pneumonia, and MAD viruses, enteric bacterial pathogens, and parasites were negative. Specific pathogen-free (SPF) transgenic animals and their nontransgenic littermates were sacrificed between postnatal days 28 (P28) and P180.

Histochemical stains—Immediately after sacrifice, the small intestine was removed en bloc, flushed with ice-cold phosphate buffered saline (PBS), fixed in 10% buffered formalin (Fisher Scientific) for 4 to 6 hours, and then washed in 70% ethanol overnight at room temperature. The intestine was embedded in plastic (JB-4 Embedding Kit, Polysciences, Warrington, Pa.), and 1 to 2 $\mu$m thick sections ("thin sections") cut from its proximal, middle, and distal thirds (these segments were arbitrarily designated duodenum, jejunum, and ileum, respectively). Alternatively, after washing in 70% ethanol, the intestine was cut open along its duodenal-ileal axis, rolled into a circle, and held in this circular configuration by mounting agar (2% agar (Sigma) in 5 % buffered formalin). Each of the resulting "Swiss rolls" was then placed in a tissue cassette, embedded in paraffin, and 5 $\mu$m-thick serial sections were prepared. Plastic- or paraffin-embedded sections were stained with hematoxylin and eosin, phloxine/tartrazine, or with Alcian blue and periodic acid Schiff (PAS) using standard protocols (Luna (ed), Manual of Histologic Staining Methods of the Armed Forces Institute of Pathology (McGraw-Hill, New York, 1968)).

Goblet cells were quantitated by counting Alcian blue/PAS-positive cells in all well-oriented jejunal crypt-villus units present in at least two non-adjacent sections cut from Swiss rolls (sections were prepared from three P28 transgenic animals and three normal littermates per pedigree). Paneth cells were likewise quantitated by counting phloxine/tartrazine-positive cells in jejunal crypts. Apoptotic cells were identified in hematoxylin and eosin-stained sections based on their characteristic morphology (Hall et al., *J. Cell Sci.* 107:3569–3577 (1994)).

To analyze the distribution of components of the microflora along the crypt-villus units of specific pathogen-free (SPF) transgenic animals and their normal littermates, mice from the various pedigrees were sacrificed at P28, P42, and P120-P180. Their small intestines were fixed 4 to 6 hours in 10% buffered formalin without prior flushing, and then cut into 1 to 2 cm segments. Each segment was embedded in paraffin, 4 to 6 $\mu$m thick sections were cut, and the sections treated with Warthin-Starry or Gram stains (Luna (ed), Manual of Histologic Staining Methods of the Armed Forces Institute of Pathology (McGraw-Hill, New York, 1968)).

Single and multilabel immunohistochemical analyses—Transgenic mice and their normal littermates were sacrificed at P28, P42, and P120-180 (n=3 to 5 per group per pedigree per time point). Some animals received an intraperitoneal injection of an aqueous solution of 5-bromo-2'-deoxyuridine (120 mg/kg, BrdU) and 5'-fluoro-2'-deoxyuridine (12 mg/kg) 1.5 to 72 hours before sacrifice. The small intestine was then removed from each animal, flushed with cold PBS, fixed in Bouin's solution for 8 hours at room temperature, treated with 70% ethanol, and 4 to 6 $\mu$m thick sections cut from paraffin-embedded Swiss rolls. Sections were then deparaffinized, rehydrated, and placed in PBS-blocking buffer (1 % bovine serum albumin, 0.3% Triton X-100 in PBS) for 20 minutes at room temperature. Slides were incubated overnight at 4° C. with the following antibodies: (i) rabbit antiserum raised against residues 4 to 35 of cryptdin-1 (the antisera reacts with purified cryptdins 1, 2, 3, and 6 (Bry et. al., *Proc. Natl. Acad. Sci.* USA 91:10335–10339 (1994); Selsted et al., *J. Cell Biol.* 118:929–936 (1992)), was diluted 1:500 in PBS-blocking buffer); (ii) rabbit antiserum to the secreted phospholipase $A_2$ encoded by Pla2g2a (also known as enhancing factor; Mulherkar et al., *Histochem.* 96:367–370 (1991); Mulherkar et al., *Biochem. Biophys. Res. Comm.* 195:1254–1263 (1993)); dilution=1:40,000); (iii) rabbit anti-human lysozyme (Dako, Santa Barbara, Calif.; specificity in the FVB/N intestine described in Bry et. al., *Proc. Natl. Acad. Sci.* USA 91:10335–10339 (1994); dilution=1:500); (iv) rabbit anti-serotonin (Incstar, Stillwater, Minn.; Roth et al., *J. Cell Biol.* 110:1791–1801 (1990); 1:8000); (v) rabbit anti-chromagranin A (Incstar; 1:10,000); (vi) rabbit anti-hGH (Dako; Roth et al., *J. Cell Biol.* 110:1791–1801 (1990); 1:2000); (vii) rabbit anti-SV40 TAg (Bry et al., *Science* 273:1380–1383 (1996); 1:2000); and (viii) goat anti-BrdU (Cohn et al., *J. Biol. Chem.* 259:12456–12462 (1984); 1:1000). Antigen-antibody complexes were detected with indocarbocyanine (Cy3)- or indodicarbocyanine (Cy5)-conjugated donkey anti-rabbit or anti-goat immunoglobulins (Ig; Jackson Immunoresearch; 1:500).

Sections were also incubated with a series of fluorescein isothiocyanate (FITC)-conjugated lectins (all obtained from Sigma, all used at a final concentration of 5 $\mu$g/mL PBS blocking buffer): (i) *Ulex europaeus* agglutinin 1 (UEA-1; carbohydrate specificity=Fuc$\alpha$1,2Gal epitopes; lineage specificity in P28-P180 FVB/N small intestine=Paneth, goblet, and enteroendocrine cells; Falk et al., *Am. J. Physiol. (Gastrointest. Liver Physiol.)* 266, G987-G1003 (1994); (ii) Peanut (*Arachis hypogaea*) agglutinin (PNA, Gal$\beta$3GalNAc; all four epithelial lineages; Falk et al., *Am. J. Physiol. (Gastrointest. Liver Physiol.)* 266, G987-G1003 (1994)); and (iii) *Dolichos biflorus* agglutinin (DBA; GalNAc$\alpha$3GalNAc and GalNAc$\alpha$3Gal epitopes; Paneth and goblet cells plus enterocytes; Falk et al., *Am. J. Physiol. (Gastrointest. Liver Physiol.)* 266, G987-G1003 (1994)).

Light Microscopy—A Molecular Dynamics Multiprobe 2001 inverted confocal microscope system was used to scan sections subjected to single and/or multi-label immunohistochemistry. Sections were also viewed and photographed using a Zeiss Axioscope.

Identification of apoptotic cells—Apoptotic cells were scored in adjacent sections of Swiss rolls, prepared from normal and CR2-TAg mice, using the terminal deoxynucleotidyltransferase (TdT) mediated, dUTP nick end labeling (TUNEL) assay, and by their morphologic appearance after staining with hematoxylin and eosin (Gavrieli et al., *J. Cell Biol.* 119:493–501 (1992); Hall et al., *J. Cell Sci.* 107:3569–3577 (1994); Wyllie et al., *Int. Rev. Cytol.* 68:251–301 (1980)). Incorporation of digoxigenin-labeled dUTP was detected using peroxidase-conjugated sheep anti-digoxigenin Fab fragments (Boehringer Mannheim, diluted 1:500 in PBS-blocking buffer) and the Vector VIP kit (Vector Laboratories). Sections were counterstained with methyl green (Zymed).

Electron Microscopy

Morphologic analysis—Three-mm$^3$ fragments were obtained from the distal jejunum of CR2-TAg transgenic mice plus their age matched littermates (n=two P28 animals/pedigree). (Note that "distal jejunum" was defined as two-thirds of the distance from the gastro-duodenal junction to the ileal-cecal junction.) Distal jejunal fragments were then fixed for 6 hours at 4° C. in 2% paraformaldehyde, 2% glutaraldehyde (prepared in PBS), washed in PBS, post-fixed for 1 hour in 2% osmium tetroxide, and stained with a solution containing aqueous uranyl acetate and lead. Samples were dehydrated in graded alcohols and embedded in Poly/Bed 812 (Electron Microscopy Sciences). One hundred nanometer-thick sections were prepared and viewed with a JOEL model 100C electron microscope.

Immunohistochemical analysis—Fragments from the distal jejunum were fixed as above, washed with PBS, dehydrated with graded ethanols, and embedded in Lowicryl (Polysciences). Fifty to seventy nanometer-thick sections were cut, placed on 100 mesh Formvar-coated grids (Electron Microscopy Sciences), and floated for 30 minutes at room temperature on a solution of Tris buffered saline (TBS)-blocking buffer (20 mM Tris, 150 mM NaCl, pH 7.4, 10% normal mouse serum, 0.3% Tween-20). Grids were then incubated for 2 hours at room temperature with rabbit anti-mouse cryptdin (see above; diluted 1:50 with TBS/5 % normal mouse serum/0.3% Tween-20), rabbit anti-mouse Pla2g2a (1:4000), or rabbit anti-hGH (Dako, 1: 100; Simon et al., *Proc. Natl. Acad. Sci.* USA 92:8685–8689 (1995)). Following washes with TBS/0.3 % Tween-20, antigen-antibody complexes were detected with 18 nm diameter colloidal gold-conjugated goat anti-rabbit IgG (Jackson Immunoresearch, diluted 1:15). Grids were counterstained with aqueous uranyl acetate and lead.

Characterization of Transgenic Mice

Light microscopic surveys of adult FVB/N small intestine disclosed that approximately 95% of all crypts present in a cross section contain cryptdin-positive cells (average=3 cells/duodenal crypt section; 5 cells/ileal crypt section). EM immunohistochemical analysis using polyclonal antibodies that recognize several members of the cryptdin family revealed that cryptdins are present in the dense core granules of granule goblet cells, intermediate cells, and Paneth cells. The EM study also indicated that these cryptdins are not expressed in any other intestinal epithelial cell type, including mature goblet cells.

Light and EM immunohistochemistry was used to define the small intestinal patterns of expression of a human growth hormone reporter in several pedigrees of P28 to P180 transgenic mice containing a cryptdin-2$^{-6500\ to\ +34}$/human growth hormone fusion gene (CR2-hGH). The results established that nucleotides –6500 to +34 of the mouse cryptdin-2 gene are active in Paneth, granule goblet, and intermediate cells and silent in all other epithelial cell types present in crypt-villus units.

Promoter-targeted expression of Simian virus T antigen (SV40 TAg) in the progenitor cells of specific lineages has been exploited to generate transgenic mouse models of specific physiologic deficiency syndromes. Physiologic deficiencies result because differentiation of these progenitors is blocked: the "entrapped" progenitors do not have the functional capacities of their terminally differentiated descendants and therefore cannot compensate for their loss (Lew et al., *Genes Dev.* 7:683–693 (1993)). SV40 TAg-stimulated amplification of normally rare progenitors also provides an opportunity to study their intrinsic properties and/or the consequences of their increased representation (for example, Lew et al., *Genes Dev.* 7:683–693 (1993); Li et al., *J. Biol. Chem.* 270:15777–15788 (1995)).

In the disclosed mice, nucleotides –6500 to +34 were used to direct expression of SV40 TAg. Three lines of CR2-TAg mice were analyzed from P28-P180. All pedigrees had identical intestinal phenotypes. The growth rates and adult body weights of transgenic mice were not significantly different from those of their normal littermates.

Staining with tartrazine, UEA1, and antibodies to cryptdins, lysozyme, and enhancing factor revealed a decrease in the number of mature Paneth cells in CR2-TAg mice (for example, 90 to 95 % at P28). EM confirmed the Paneth cell ablation.

SV40 TAg-positive epithelial cells were distributed along the length of the crypt-villus axis. These cells were most abundant in the crypts and lower half of the villus. SV40 TAg levels decreased as cells moved to the upper half of the villus. SV40 TAg-positive villus epithelial cells were also UEA-1 positive. The UEA-1I/SV40 TAg-positive cells were members of the goblet cell lineage. CR2-TAg animals exhibit a statistically significant 2 to 3 fold increase in the number of Alcian blue/PAS-positive goblet cells per duodenal, jejunal, or ileal villus section ($p<0.05$; reference control=age matched normal littermates). Pulse labeling with BrdU 1.5 hours prior to sacrifice revealed that production of SV40 TAg is associated with re-entry of these villus goblet cells into S-phase.

EM immunohistochemical studies provided further insights about the origins of this amplified goblet cell population. Analyses of distal jejunal crypts from CR2-TAg mice and their normal littermates disclosed a marked amplification of cryptdin- and phospholipase $A_2$ (Pla2g2a)-positive "intermediate" and granule goblet cells in transgenic crypts. Intermediate cells were found in the lower two thirds of these crypts. The diameter of the granule's electron dense core diminishes and the relative area occupied by its mucin increases as cryptdin- and phospholipase $A_2$-positive cells occupy the upper regions of transgenic crypts, resulting in an amplified population of granule goblet cells positioned in the upper crypt/lower villus. SV40 TAg- and UEA1-positive goblet cells in the upper half of the villus lack dense core granules, do not contain the secreted phospholipase A or cryptdin, and have the morphologic, histochemical, and immunohistochemical features of normal mature common goblet cells. These results suggest a sequence of "differentiation" involving transformation from intermediate to granule goblet to "mature" common goblet cell.

Even though the ablation of mature Paneth cells by CR2-TAg was accompanied by an amplification of intermediate and granule goblet cells, the space occupied at the crypt base by Paneth cells was occupied in CR2-TAg mice by "crypt base columnar cells." These crypt base columnar cells lack SV40 TAg but incorporate BrdU. Crypt base columnar cells are normally interspersed among Paneth cells and constitute 60 to 70% of the cells that populate the bottom three cell layers of duodenal, jejunal, and ileal crypts (Cheng and Leblond, *Am. J. Anat.* 141:461–480 (1974)). Previous [$^3$H]thymidine labeling/EM radioautography studies indicated that (i) their residence time at the crypt base after entering S-phase is just a few hours; (ii) they migrate up and out of duodenal, jejunal, and ileal crypts within 3–4d; and (iii) they differentiate into enterocytes (Cheng and Leblond, *Am. J. Anat.* 141:461–480 (1974)).

Macro- and microscopic surveys of the intestines of P28-P180 mice from the three CR2-TAg pedigrees indicated that expression of this viral oncoprotein did not lead to the development of intestinal neoplasms (n=40 animals). The increased levels of apoptosis noted in the crypts of CR2-TAg mice suggests that some differentiating Paneth cells could be cleared by this mechanism, induced as a consequence of their SV40 TAg-induced proliferation. There is precedent for this elsewhere in the crypt-villus axis: forced expression of SV40 TAg in post-mitotic FVB/N villus enterocytes using a different promoter results in their pRB-dependent re-entry into the cell cycle and the induction of a p53-independent apoptosis (Chandrasekaran et al., *J. Biol. Chem.* 271:28414–28421 (1996)). Augmented apoptosis of SV40 TAg+ Paneth cells may explain, in part, why CR2-TAg mice do not develop intestinal neoplasms.

Despite the production of prostate tumors in CR2-TAg mice, neoplasms in intestinal tissue is not increased in these animals. A Leu Stop substitution at codon 850 in the 2845 residue mouse Apc protein is associated with the development of multiple intestinal neoplasms (Min; Su et al., *Science* 256:668–670 (1992); Moser et al., *Science* 247:322–324 (1990)). Comparable germline mutations in the human APC gene also leads to multiple gut adenomas (familial adenomatous polyposis). Mom1 is a semi-dominant modifier of tumor multiplicity in Minl+ animals located on mouse chromosome 4 (Dietrich et al., *Cell* 75:631–639 (1993)). Genetic studies indicate that Pla2g2a is a candidate gene for Mom1 (MacPhee et al., *Cell* 81:957–966 (1995); Gould et al., *Genetics* 144:1769–1776 (1996); Gould et al., *Genetics* 144:1777–1785 (1996)). Two Pla2g2a alleles have been described. One allele contains a frameshift mutation (Mom-1$^S$) and is encountered in C57BL/6J and 129/Sv-Pas mice. The other allele does not contain the mutation (Mom1$^R$) and is found in AKR/J, MA/MyJ, BALB/cByJ, and Mm. castaneus animals (Gould et al., *Genetics* 144:1777–1785 (1996)). Mom1$^S$ is associated with 4–8 fold greater number of intestinal adenomas. Current evidence indicates that a Min adenoma arises within a small intestinal crypt and that the initiated cell may be the stem cell or one of its immediate descendants. The mechanism by which the secreted phospholipase $A_2$ encoded by Pla2g2a could influence initiation or progression is unclear at present. Experiments indicate that neither a marked reduction in Pla2g2a in the crypt nor an expansion of the population of intermediate and granule goblet cells that produce this phospholipase $A_2$ are associated with apparent changes in the properties of the crypt stem cell or its descendants.

Targeting potential regulators of tumorigenesis to the apical secretory apparatus of Paneth cells using nucleotides −6500 to +34 of the mouse cryptdin-2 gene could result in their export to the stem cell zone, thereby testing their effects in Minl+ or other mouse models. These latter experiments illustrate how the Paneth cell and the CR2 gene regulatory elements can be as a tool for delivering a variety of molecules to a critical region of the crypt where decisions about proliferative status and lineage allocation are made.

Publications cited herein and the material for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A transgenic mouse whose genome comprises a nucleic acid construct, wherein the construct comprises nucleic acid encoding a protein operably linked to cryptdin-2 gene transcription regulatory elements, and wherein the nucleic acid is expressed in prostate cells of the transgenic mouse such that the protein is produced at detectable levels.

2. Prostate cells isolated from the transgenic mouse of claim 1, wherein the cells express the nucleic acid encoding the protein.

3. A transgenic mouse whose genome comprises a nucleic acid construct, wherein the construct comprises nucleic acid encoding an oncogene protein operably linked to cryptdin-2 gene transcription regulatory elements, and wherein the nucleic acid is expressed in prostate cells of the transgenic mouse such that the transgenic mouse develops prostate tumors.

4. The transgenic mouse of claim 3 wherein the oncogene protein is SV40 T antigen.

5. The transgenic mouse of claim 3 wherein the prostate tumors are androgen independent.

6. The transgenic mouse of claim 3 wherein the prostate tumors metastasize.

7. The transgenic mouse of claim 3 wherein cells in the prostate tumors are from neuroendocrine cell lineages and exhibit neuroendocrine differentiation.

8. Prostate cells isolated from the transgenic mouse of claim 3, wherein the cells express the nucleic acid encoding the oncogene protein.

9. The cells of claim 8, wherein the cells are established as a cell line.

10. A method of testing compounds for an effect on prostate tumors, the method comprising, a) administering the compound to be tested to a transgenic mouse whose genome comprises a nucleic acid construct, wherein the construct comprises nucleic acid encoding an oncogene protein operably linked to cryptdin-2 gene transcription regulatory elements, and wherein the transgenic mouse develops prostate tumors; and b) comparing one or more characteristics of the prostate tumors in the transgenic mouse to which the compound was administered with the same one or more characteristics of the prostate tumors in the transgenic mouse to which the compound has not been administered, wherein a difference in one or more of the one or more characteristics indicates that the compound has an effect on prostate tumors.

11. The method of claim 10, wherein the oncogene protein is SV40 T antigen.

12. The method of claim 10 wherein the prostate tumors are androgen independent.

13. The method of claim 10 wherein the prostate tumors metastasize.

14. A method of identifying markers associated with prostate cancer, the method comprising, comparing the presence, absence, or level of expression of genes in prostatic tissue from a transgenic mouse and prostatic tissue from a second mouse, wherein the genome of the transgenic mouse comprises a nucleic acid construct and the genome of the second mouse does not comprise the nucleic acid construct, wherein the construct comprises nucleic acid encoding an oncogene protein operably linked to cryptdin-2 gene transcription regulatory elements, and wherein the nucleic acid is expressed in the prostate cells of the transgenic mouse such that the transgenic mouse develops prostate tumors, wherein the difference between the transgenic mouse and the second mouse in the presence, absence, or level of expression of a gene indicates that the expression of the gene is a marker associated with prostate cancer.

15. The method of claim 14, wherein the oncogene protein is SV40 T antigen.

16. The method of claim 14 wherein the prostate tumors are androgen independent.

17. The method of claim 14 wherein the prostate tumors metastasize.

\* \* \* \* \*